United States Patent
Gündogdu

(10) Patent No.: US 10,758,307 B2
(45) Date of Patent: Sep. 1, 2020

(54) HAIR REMOVAL DEVICE

(71) Applicant: MAVILAB YAZILIM MEDIKAL LAZER MAKINA IMALATI SANAYI VE TICARET ANONIM SIRKETI, Ankara (TR)

(72) Inventor: Sinan Gündogdu, Ankara (TR)

(73) Assignee: MAVILAB YAZILIM MEDIKAL LAZER MAKINA IMALATI SANAYI VE TICARET ANONIM SIRKETI, Ankara (TR)

( * ) Notice: Subject to any disclaimer, the term of this patent is extended or adjusted under 35 U.S.C. 154(b) by 204 days.

(21) Appl. No.: 15/771,410

(22) PCT Filed: Nov. 1, 2016

(86) PCT No.: PCT/EP2016/076296
§ 371 (c)(1),
(2) Date: Apr. 27, 2018

(87) PCT Pub. No.: WO2017/076830
PCT Pub. Date: May 11, 2017

(65) Prior Publication Data
US 2018/0344403 A1  Dec. 6, 2018

(30) Foreign Application Priority Data

Nov. 2, 2015 (EP) .................................... 15192556

(51) Int. Cl.
*A61B 18/20* (2006.01)
*A61B 90/00* (2016.01)
(Continued)

(52) U.S. Cl.
CPC ............ *A61B 18/203* (2013.01); *A61B 90/37* (2016.02); *A61B 2017/00752* (2013.01);
(Continued)

(58) Field of Classification Search
CPC ................. A61B 18/203; A61B 90/37; A61B 2017/00752; A61B 2090/309;
(Continued)

(56) References Cited

U.S. PATENT DOCUMENTS

2006/0095099 A1  5/2006  Shanks et al.
2014/0107635 A1  4/2014  Poran et al.

FOREIGN PATENT DOCUMENTS

DE     10013910 A1   10/2001
EP      1031324 A1    8/2000
(Continued)

OTHER PUBLICATIONS

Jafarizadeh Saeid et al, "A Novel Infrared Touch Sensing Using K-Nearest Neighbor Algorithm", ICCKE 2013, IEEE, Oct. 31, 2013, pp. 252-256, XP032531177, DOI: 10.1109/ICCKE. 2013. 6682805.

*Primary Examiner* — Scott M. Getzow
(74) *Attorney, Agent, or Firm* — Bayramoglu Law Offices LLC

(57) ABSTRACT

The present invention proposes a laser hair removal device handheld head (1) provided with a camera objective (13), one or more first light source (10), and a transparent member (12) for being placed onto a skin region to be subjected to laser hair removal, wherein the first light source (10) and transparent member (12) being configured to provide frustrated total internal reflection (FTIR) based images of the skin region. The present invention further proposes a laser hair removal method.

11 Claims, 4 Drawing Sheets

(51) Int. Cl.
*A61B 17/00* (2006.01)
*A61B 90/30* (2016.01)
*A61B 18/00* (2006.01)

(52) U.S. Cl.
CPC ............... *A61B 2018/00476* (2013.01); *A61B 2090/049* (2016.02); *A61B 2090/309* (2016.02); *A61B 2090/373* (2016.02)

(58) Field of Classification Search
CPC ........ A61B 2090/373; A61B 2090/049; A61B 2018/00476
See application file for complete search history.

(56) References Cited

FOREIGN PATENT DOCUMENTS

| | | |
|---|---|---|
| TR | 2012/13577 | 11/2012 |
| WO | 2005065565 A1 | 7/2005 |
| WO | 2005102201 A1 | 11/2005 |
| WO | 2009142758 A1 | 11/2009 |

HAIR REMOVAL DEVICE

CROSS REFERENCE TO THE RELATED APPLICATIONS

This application is the national phase entry of International Application No. PCT/EP2016/076296, filed on Nov. 1, 2016, which claims priority from EP Patent Application 15192556.7, filed on Nov. 2, 2015, the entire contents of which are incorporated herein by reference.

TECHNICAL FIELD

The present invention relates to a hair removal device with pattern recognition and visualization techniques.

BACKGROUND

Optical hair removal devices provide high-energy laser beams with wavelengths absorbable at hair roots, at pulses having durations usually within a range between 1 ms and 500 ms (ms: milliseconds). Upon being subjected to laser beams, hair roots get heated and thus damaged. Permanent depilation can be achieved by several repetitions of such application.

WO 2005/102 201 A1 describes a hair removal device aiming for a certain distance between skin and a contact plate for obtainment a reliable hair removing of locally curved regions of skin.

US 2006/0 095 099 A1 describes a stand-alone laser device comprising a support structure enabling a patient to be scanned without moving the laser energy source.

EP 1 031 324 A1 describes a laser depilation apparatus for alleviating damage to surrounding tissues of treated hair follicles.

TR 2012/13577 describes a laser hair removal device aiming for precise hair removal notwithstanding the optical contrast around target hair.

Some of the main problems encountered in known laser hair removal technology can be summarized as follows:

In order to obtain an efficient hair removal by selective damaging of hair roots, target hair root shall absorb more light in comparison with surrounding skin regions. But the light absorbing pigment melanin is present in hair roots and also in skin. Therefore in low-contrast color combination cases of pale skin with light hair, or dark skin with dark hair, sufficient optical contrast for selective damaging of hair cannot be easily achieved. As a result, even maximum values of light energy provided onto hairy skin cannot damage target hair without damaging the surrounding skin as well; and either permanent hair removal cannot be achieved, or a large number of sessions is required for permanent hair removal.

Hair removal necessitates heating of target hair root to a threshold temperature for permanent damage thereof. Below such temperature, heating provokes repair mechanisms thus the target hair root builds up instead of getting damaged. In cases of above-mentioned low-contrast color combinations, or similarly, in skin regions where relatively thick and thin hair roots are present in a mixed manner such as at the face of a patient, thin hair builds up due to said mechanism; and this phenomenon is referred to as 'paradoxial hypertrichosis'.

Especially patients having darker colored skin experience widespread sharp aches on their skin around laser-treated areas thereof. This presumably occurs due to high absorbance of light energy by high concentration of melanin in dark skin.

In cases where the amount of light energy per unit area (i.e. fluence) is arranged and calculated imprecisely and improperly, the risk of ambustion arises at wide skin portions.

SUMMARY

Primary object of the present invention is to overcome the abovementioned shortcomings of the prior art.

Another object of the present invention is to provide a laser hair removal device and method which is efficient at low optical contrast skin/hair color combinations.

Yet another object of the present invention is to provide a laser hair removal device and method which eliminates paradoxical hypertrichosis.

Another object of the present invention is to minimize aches caused by inefficient laser hair removal.

Further an object of the present invention is to eliminate ambustion risk of wide skin regions due to inefficient laser hair removal.

The present invention proposes a laser hair removal device handheld head provided with a camera objective, one or more first light source, and a transparent member for being placed onto a skin region to be subjected to laser hair removal, wherein the first light source and transparent member being configured to provide frustrated total internal reflection (FTIR) based images of the skin region. The present invention further proposes a laser hair removal method.

BRIEF DESCRIPTION OF THE DRAWINGS

The figures, whose brief explanation are herewith provided, is solely intended for providing a better understanding of the present invention and is as such not intended to define the scope of protection or the context in which said scope is to be interpreted in the absence of the description.

DETAILED DESCRIPTION

Figure 1:
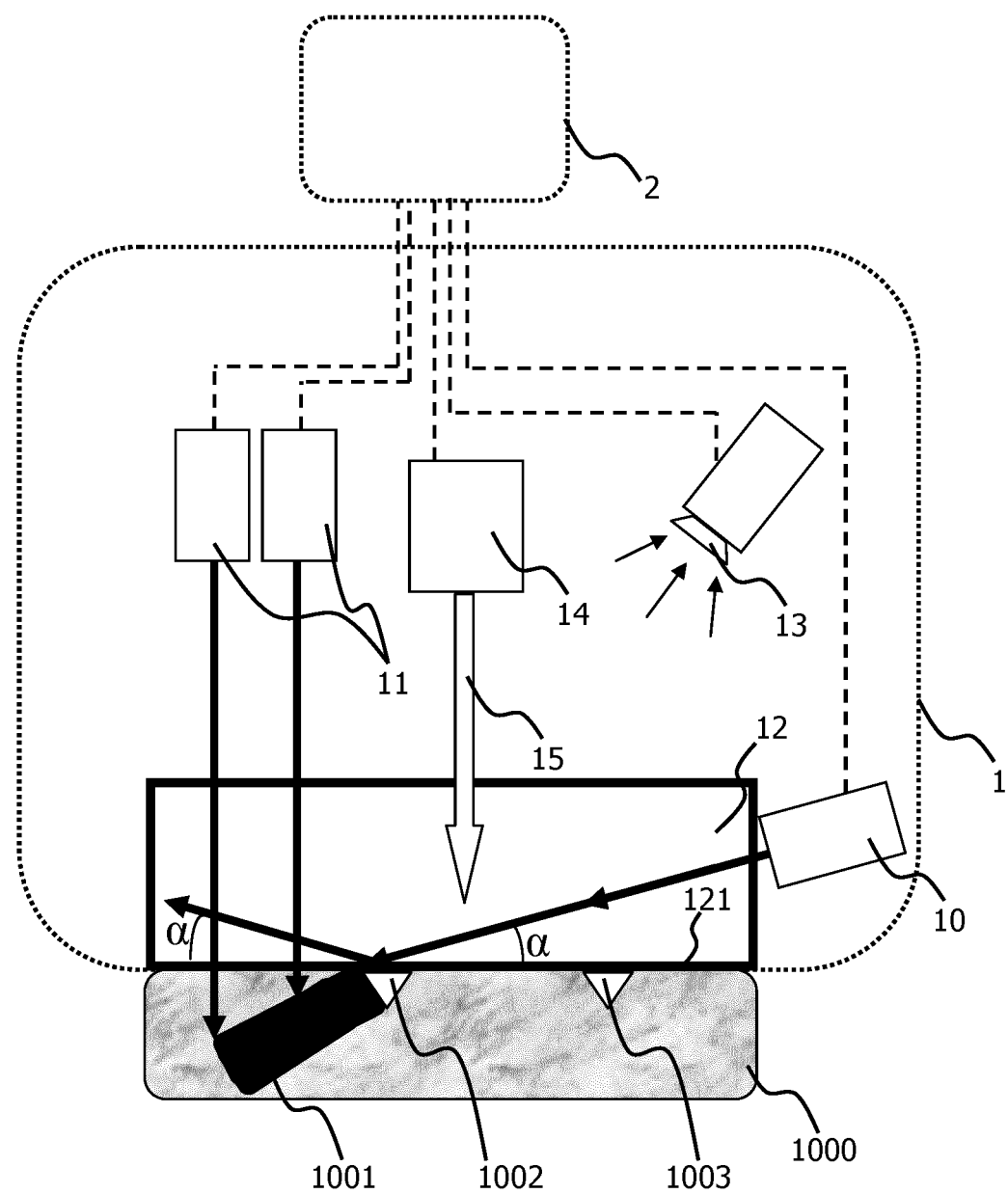
FIG. 1 is shows a schematic representation of an embodiment of the hair removal device according to the present invention.
Figure 2:
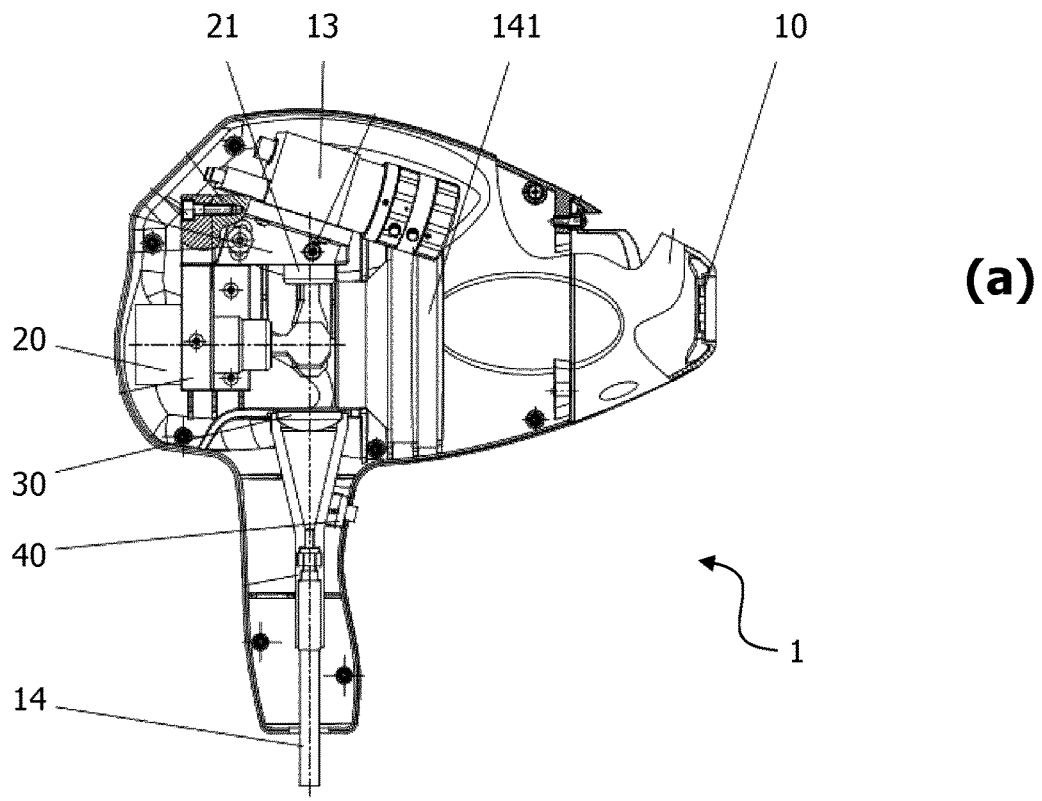
FIG. 2 shows a section view (a), and a front view (b) of an embodiment of the laser hair removal device handheld head according to the present invention.
Figure 2:
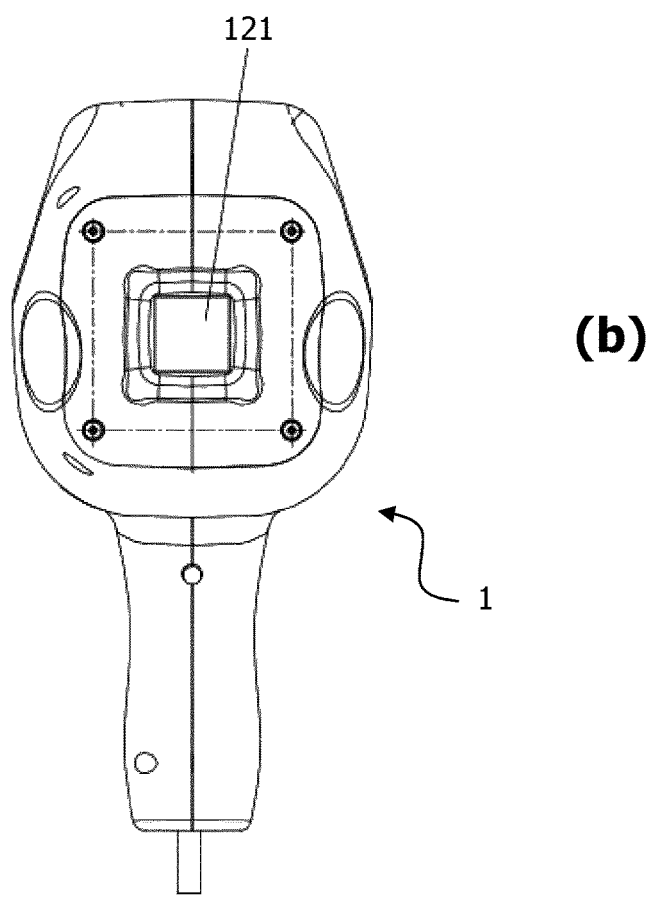
Figure 3:
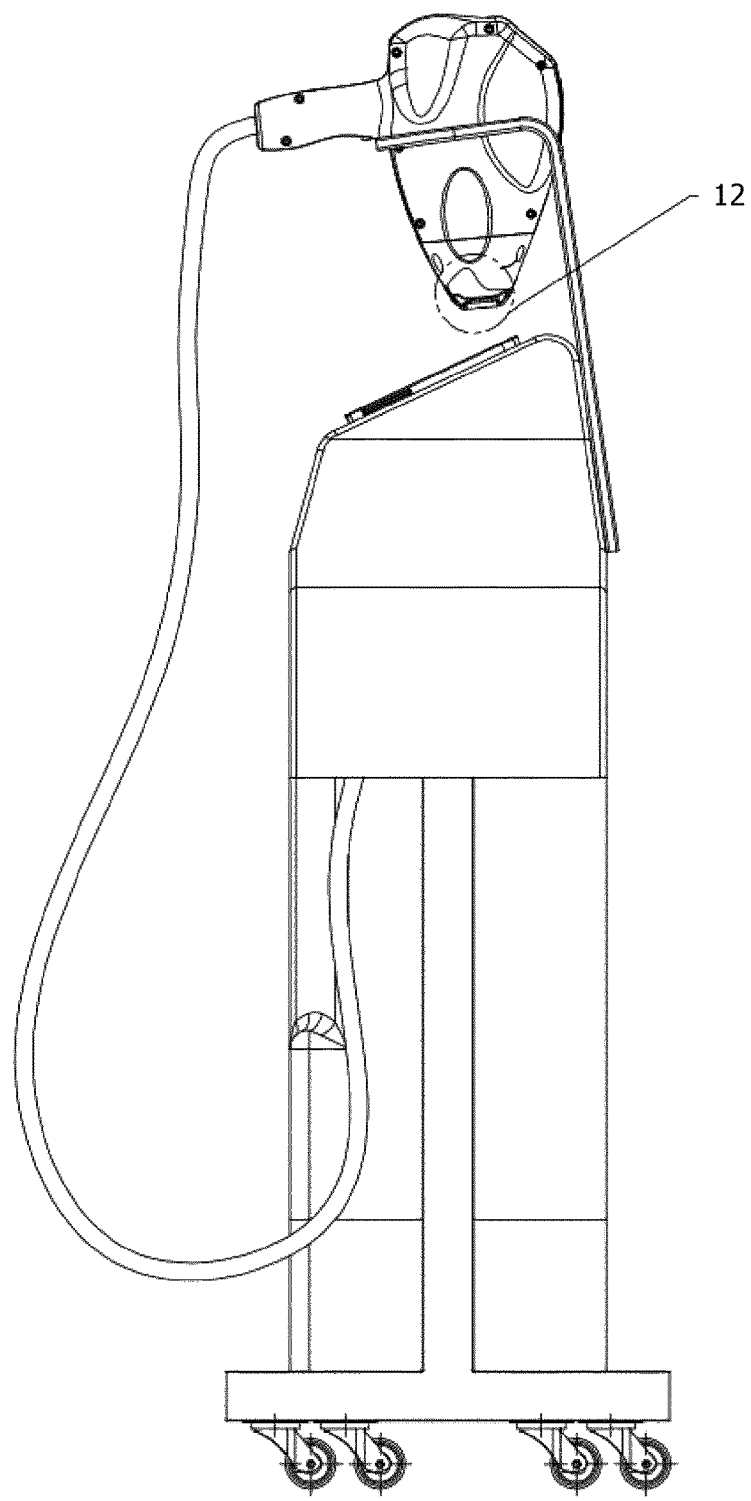
FIG. 3 shows an exemplary layout of the laser hair removal device handheld head connected to the hair removal device according to the present invention.

Referring now the figures outlined before, the present invention proposes a laser hair removal device handheld head (1) provided with a camera objective (13), one or more first light source (10) and with a transparent member (12) for being placed onto a skin region to be subjected to laser hair removal, the first light source (10) and transparent member (12) being configured to, in use, provide frustrated total internal reflection (FTIR) based images of the skin region.

Such configuration can be obtained by angular arrangement between the light beams from the light source, and skin contact plane of the transparent member, wherein the angle is below a critical angle determinable by e.g. Fresnel Equation such that light beams completely reflect from the skin contact plane. The critical angle is the angle between a skin contacting surface (121) and a light beam from the first light source (10), below which total internal reflection occurs; thus, for obtainment of FTIR-based images, the angle (a) between the light beams from the first light source and the skin contacting surface (121) of the transparent member (12) is configured to have a value not greater than the critical angle. Maximum angle value suitable for this aim can be determined by a skilled person in the art of optical physics, in accordance with refraction-related correlations of optics (e.g. Fresnel Equations).

The head (1) preferably further comprises a second light source (11) configured to provide a series of different wavelengths preferably within a range between 400 nm and 1060 nm, configured to, in use, direct light beams through the transparent member onto the skin region. The second light source (11) preferably comprises a plurality of light emitting diodes (LEDs).

Figure 4:
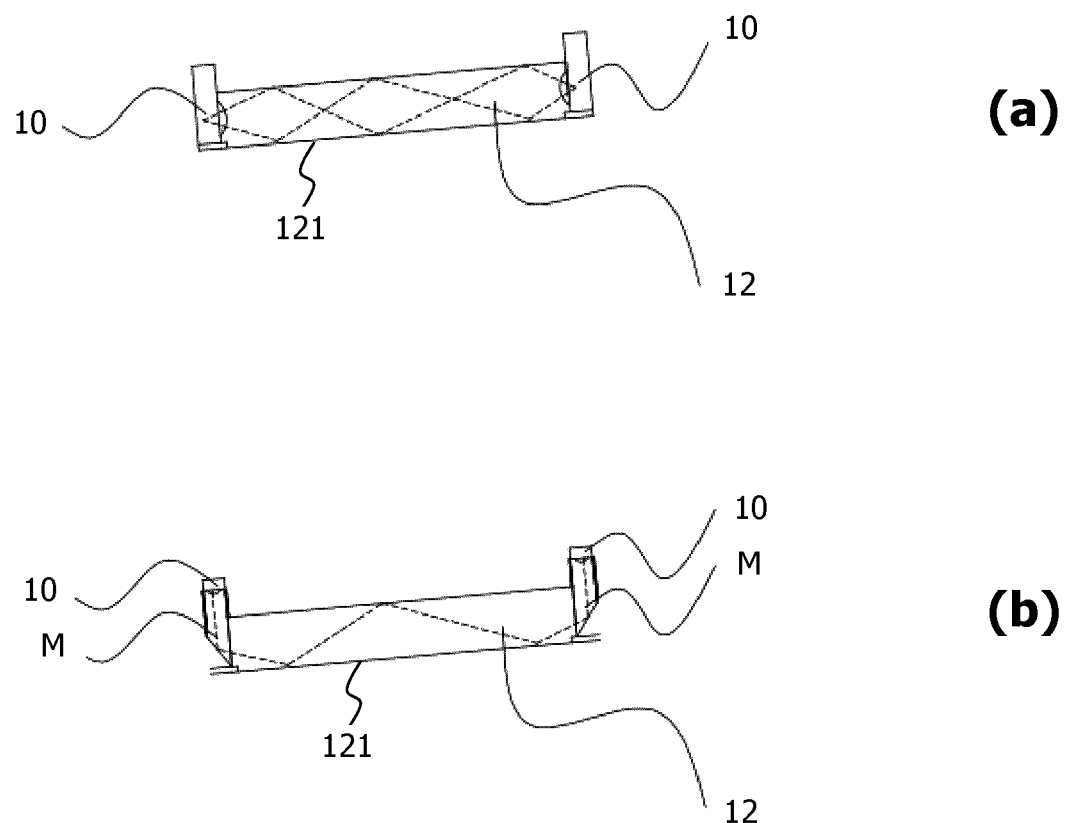
FIG. 4 represents two preferred layouts of light sources with respect to the transparent member for obtainment of FTIR based images: (a) without mirror, and (b) with mirrors.

The head (1) preferably further comprises one or more galvo mirror (21, 22) configured to direct laser beams from a laser source (14) towards the transparent member (12). The laser source (14) is preferably a laser diode. In FIG. 4, the numeral 141 corresponds to laser optic for proper orientation of laser beams; and 30 corresponds to a lens for focalization of laser beams.

The present invention further provides a laser hair removal device (2) configured to be in optical, data and electrical communication with the head (1), said device (2) having computing abilities or being connectable to a computer such that, in use, the FTIR-based digital image data being introduced for calculation of hair roots orientation data (with respect to corresponding skin surface) using k-nearest neighbor (kNN) and support vector machine (SVM) algorithms.

In other words, For determination of in-depth orientation of a hair root (1001) below surface of a skin region (1000), the head (1) preferably comprises a second light source (11) providing a series of different wavelength light beams, such that said light beams traverse the transparent member (12), and penetrate into the skin region (1000) into different penetration depths in accordance with corresponding wavelength values. As a result, images showing the orientation of a hair root (1001) beyond the skin contacting surface (121) and thus below the skin surface can be obtainable by an objective (13) directed towards the transparent member (12). Such images serve for determination of orientation of each hair root (1001) to be subjected to laser beams. For compensation of errors due to light scattering arising with increasing light penetration depths in the skin region, k-nearest neighbor (kNN) and support vector machine (SVM) algorithms are preferably employed.

FIG. 1 shows a schematic representation of an embodiment according to the present invention, emphasizing the light beams from first and second light sources (10, 11), laser beam (15) from the laser source (14), camera objective (13), communication thereof with the hair removal device (2), the contact between the transparent member (12) and the skin region (1000) to be subjected to laser hair removal.

For provision of FTIR-based images to the objective (13), one or more first light source (10) are configured to provide light beams to a skin contacting plane (121) of the transparent member (12) with an aspect angle (a) below the critical angle which is determinable according to e.g. Fresnel Equations. As a result, the light beams from the first light source (10) completely reflects from the skin contacting plane (121) such that dented parts (i.e. openings of hair roots (1002) and pores (1003)) on a skin region (1000) subjected to such imaging, are identifiable by a camera objective (13), since such dented parts cannot mechanically contact to the skin contacting plane (121) even when the transparent member (12) is pressed onto the skin region (1000); and FTIR-based images and patterns showing dented parts such as hair root openings and pores can be thus obtained. These images serve for surface mapping, i.e. for locating each hair root opening (1002) and pore (1) on a skin region (1000) to be subjected to laser beams for hair removal.

FIG. 4 proposes examples for light source—transparent member configurations for being employed in the head according to the present invention. In the embodiment given in FIG. 4(a), a plurality of first light sources (10) placed reciprocally, and outer planes of the transparent member (12) perpendicular to the skin contacting plane (121) are preferably black for fully absorbing the light beams from the first light sources (10). In the embodiment given in FIG. 4(b), light beams from a plurality of first light sources (10) are angularly placed with respect to the first light sources and the skin contacting plane (121), and outer planes of the transparent member (12) perpendicular to the skin contacting plane (121) are preferably reflective for fully reflecting the light beams from the first light sources (10) to the inside of the transparent member.

Accordingly, laser beams (15) can be accurately directed onto dented parts including hair root openings (1002) and pores (1003), preferably via one or more galvo mirror (20, 21) located in the head (1).

The following considerations lead to the device and a corresponding method according to the present invention:

Laser beams focused onto a small area corresponding to a single hair root, are provided onto a skin region to be subjected to hair removal, said beams preferably having a diameter within a range between 100 to 300 micrometers. The rest of skin remains basically unaffected by the beams via focused and accurately transferring energy onto hair roots sufficient for damaging thereof, even at low-contrast skin/hair color combinations such as dark skin with dark hair, or pale skin with light hair.

Unwanted build up in thin hair roots can be avoided by selective heating and damaging of only thick hair roots, thus the number of treatment sessions required for permanent hair removal is minimized.

Laser beams can be mainly focused on required spots (e.g. onto thick hair roots) and the rest of the skin remains mainly unaffected by laser beams; as a result, the ache felt by the patient is minimized.

Even in case of erroneous operation by transferring higher levels of energy then required, the ambustion risk of wide regions of skin is eliminated.

In a preferred embodiment/application according to the present invention, location information of target hair roots below skin surface are obtained by taking a series of images of a target skin region by subjecting such skin region to a second light source (11) having different wavelengths; said wavelengths vary preferably within a range between 400 nm and 1060 nm (nanometers). Each wavelength has different depths of penetration, e.g. light having a wavelength of 400 nm cannot penetrate deeper than a few hundred microns, light with 800 nm of wavelength can penetrate into skin to about 3 mm of depth; thus a series of penetration depths is obtained by such variation of different wavelength light sources (11). Yet, by higher penetration depths, the scattering of the light within the skin causes escalation in difficulty at obtainment of accurate images. Therefore the software (or calculation methods used throughout the algorithm) used in recognition of hair roots is preferably subjected to modification. Such modification is applied using kNN and SVM algorithms and to this end, one or more value calculated using the images are introduced as modification data; said values are selected from the list consisting of histogram distribution, intensity variance, contrast, and number of pixels below and above a mean value. The latter property referred to as 'number of pixels below and above a mean value' can be determined for each point by

- designation of a rectangular region around a point as center of the rectangular region, the rectangular region preferably being a square with dimensions within a range between 8×8 pixels and 16×16 pixels;
- capturing of digital image of the region, followed by calculation of pixel values for each pixel therein;
- enumeration of pixels having greater value than said mean pixels value, for each rectangular region.

The above sequence can be repeated for each pixel in the rectangle, or camera capture of a skin region can be divided into grids (e.g. square grids a square with dimensions within a range between 8×8 pixels and 16×16 pixels) and calculated for each grid. Thus, the present invention provides enhanced pattern recognition, which is tailored for obtainment of improved classification of thick hair roots to be removed. Hair root and skin regions to be treated are camera-recorded, and the above mentioned attribute values (e.g. entropy, histogram distribution, intensity variance, contrast, and numbers of pixels below and above a certain mean value) are calculated. Afterwards, the calculated values are used for recognition of hair roots to be targeted, using k-nearest neighbor (kNN)) and support vector machine (SVM) algorithms. The success and accuracy of the proposed method gets higher by employing higher number of calculated values selected from the above list, since higher amount of information can be thus obtained for accurate recognition of a hair root.

The present application further proposes a hair removal method comprising following steps:

a. Shaving a skin region to be subjected to hair removal,
b. Placing a handheld head of a hair removal device onto said skin region by pressing the head thereonto, such that a transparent member on the head touches the skin region; the head further comprising one or more first light source being configured to produce frustrated total internal reflection (FTIR) based digital images of the skin region by angular arrangement between the light source and the transparent member,
c. Capturing FTIR based images, such that topography of said skin region including dented parts on the skin are identified; said dented parts including hair roots and pores;
d. Communication of hair root location data and preferably pores location data to the microcontroller, said data being used by the microcontroller for subjecting hair roots and preferably pores on the skin region with sufficient duration and intensity of laser beams for permanent removal thereof within one or more session, by orientation of galvo mirrors accordingly.

Preferably, the method comprises a further step including direction of a series of different wavelength light beams through the transparent member onto the skin, said direction being controlled by a computer communicating by a microcontroller of the hair removal device; said wavelengths being preferably within a range between 400 nm and 1060 nm; thus determining hair roots orientation below the skin surface. Further preferably, said step is followed by calculation of one or more value from captured images, said values being selected from a list consisting of histogram distribution, intensity variance, contrast, and numbers of pixels below and above a certain mean value, for use as modification data to be used in k-nearest neighbor (kNN) and support vector machine (SVM) algorithms; for compensation of effects of light scattering phenomenon at different skin depths.

Preferably, when the image capturing of a skin region is finished, an audio signal is produced by the hair removal device, thus it is made sure that an operator of the device can safely proceed to image capturing of another skin region.

The operation can preferably be commenced by activating a trigger or switch (40) (e.g. button) on the handheld head. Alternatively, the trigger can be e.g. a paddle in electrical and data communication with the device.

In a preferred embodiment according to the present invention, the head and/or the hair removal device is connectable to a screen configured to provide visually monitoring of skin region to be subjected to laser hair removal. More preferably, said monitor is positioned on the head (1) and/or on the device (2).

A hair root opening (1002) is distinguishable from a pore (1003) by observing (visually or digitally) color differences in vicinity of a dented part when subjected to light beams from the second light sources (11). Here, in case where there is no color difference available in proximity of a dented region under the skin surface, such dented region corresponds to a pore (1003). In an opposite case where obtained color varies in proximity of a dented part under the skin surface, such dented part can be treated as a hair root opening; and laser beams can be applied preferably starting from the coordinates of hair root opening along the hair root orientation determined using the second light sources (11).

To this end, the method according to the present invention preferably further comprises distinction of pores from hair roots by taking color differences in vicinity of dented parts under the skin surface into consideration when subjected to different wavelength light beams; such that

- a dented part is identified as a pore, when no color difference is observed in proximity of a dented region under the skin surface, and
- a dented part is identified as a hair root opening, when a color difference is observed in proximity of a dented region under the skin surface.

According to the present invention, in other words, a surface mapping is applied on the skin via a transparent member (e.g. an element made of glass) using frustrated total internal reflection (FTIR), by which the topography of the skin can be obtained. This provides accurate location of pores and hair outlets on shaved skin, notwithstanding the low values of optical contrast between hair and skin. Further preferably, orientation information of target hair roots below skin surface are obtained by augmenting the information concerning the hair outlet location with location information of target hair roots obtained as described above. This provides improved accuracy at locating of target hair roots. Furthermore, using this augmented information, it is rendered possible to obtain a through damage of target hair root which is probably inclined with respect to skin surface, from its outlet to a its distal end therefrom. Further treatment of the skin is also enabled by selective burning the pores on the skin, for obtaining improved smoothness thereof. Moreover, with this approach, selective and accurate burning/damaging of sweat glands is also obtainable for treatment of sweating disorders.

The transparent member, which in use serves as a contact area between skin and the device, enables a standard size and focused imaging, and it further enables immobilization of the device head with respect to target skin area providing proper scanning thereof after imaging.

With the laser hair removal method according to the present invention, the following are achieved:
- enhancement of success in locating hair roots on various skin types,
- new imaging techniques for higher accuracy location of target hair roots,
- improved immobilization of the hair removal device with respect to skin, throughout imaging and laser application processes.

Thus, generally, the following objects are achieved by the present invention:
- the abovementioned shortcomings of the prior art are overcome,
- efficient laser hair removal at low optical contrast skin/hair color combinations is provided,
- paradoxial hypertrichosis is eliminated,
- aches because of inefficient laser hair removal are minimized,
- ambustion risk of wide regions of skin is eliminated.

The invention claimed is:

1. A laser hair removal device comprising: a handheld head provided with a camera objective;
wherein, the handheld head comprises one or more first light sources, and a transparent member for being placed onto a skin region to be subjected to laser hair removal, wherein the first light source and the transparent member are configured to provide frustrated total internal reflection (FTIR) based images of the skin region by angular arrangement between the first light source and the transparent member; the handheld head comprising a second light source, which is different from the first light source, by providing a series of different wavelength light beams, the laser hair removal device is configured to calculate hair roots orientation data based on data related to the FTIR-based images using k-nearest neighbor (kNN) and support vector machine (SVM) algorithms.

2. The laser hair removal device according to claim 1, wherein the series of different wavelengths are within a range between 400 nm and 1060 nm, wherein the second light source is configured to direct the light beams through the transparent member onto the skin region.

3. The laser hair removal device according to claim 2, wherein the second light source comprises a plurality of light emitting diodes.

4. The laser hair removal device according to claim 1, wherein the handheld head further comprises one or more galvo mirrors configured to direct laser beams from a laser source towards the transparent member.

5. The laser hair removal device according to claim 4, wherein the laser source is a laser diode.

6. A non-therapeutical laser hair removal method comprising the sequential steps of:
a. shaving a skin region to be subjected to hair removal,
b. placing a handheld head of a hair removal device onto said skin region by pressing the handheld head thereonto, such that a transparent member on the handheld head touches the skin region; the handheld head further comprises one or more light sources being configured to produce frustrated total internal reflection (FTIR) based digital images of the skin region by an angular arrangement between the light source and the transparent member,
c. capturing FTIR based images, such that topography of said skin region including dented parts on the skin are identified; the dented parts include hair roots and pores,
d. communicating hair root location data and pores location data to a microcontroller, said data being used by the microcontroller for subjecting hair roots and pores on the skin region with sufficient duration and intensity of laser beams for permanent removal thereof within one or more sessions, wherein the method further comprises directing a series of different wavelength light beams through the transparent member onto the skin, said direction being controlled by a computer communicating by a microcontroller of the hair removal device; said wavelengths being within a range between 400 nm and 1060 nm; thus determining hair roots orientation below the skin surface, and wherein the step (d) is followed by compensation of light scattering phenomenon based errors at different skin depths, by calculation of one or more values from captured images; said values being selected from a list consisting of entropy, histogram distribution, intensity variance, contrast, and numbers of pixels below and above a certain mean value, for use as modification data to be used in k-nearest neighbor (kNN) and support vector machine (SVM) algorithms.

7. The method of claim 6, wherein the laser beams have a diameter within a range between 100 micrometers and 300 micrometers.

8. The method of claim 7, further comprising distinction of pores from hair roots by taking color differences in vicinity of the dented parts under the skin surface into consideration when subjected to the different wavelength light beams; such that
- a dented part is identified as a pore, when no color difference is observed in proximity of a dented region under the skin surface, and
- a dented part is identified as a hair root opening, when a color difference is observed in proximity of a dented region under the skin surface.

9. The method of claim 6, wherein the laser beams are directed using one or more galvo mirrors.

10. The method of claim 8, wherein number of pixels below and above a certain mean value are determined by
- designation of a rectangular region around a point as center of the rectangular region, the rectangular region being a square with dimensions within a range between 8×8 pixels and 16×16 pixels;
- capturing of digital image of the region, followed by calculation of pixel values for each pixel therein;
- enumeration of pixels having greater value than said mean pixels value, for each rectangular region.

11. The method of claim 6, wherein the skin region is monitored for visually following the hair removal session on a monitor in communication with the handheld head.

* * * * *